United States Patent [19]

Verdicchio

[11] Patent Number: 4,726,915

[45] Date of Patent: Feb. 23, 1988

[54] DETERGENT COMPOSITIONS

[75] Inventor: Robert J. Verdicchio, Succasunna, N.J.

[73] Assignee: Johnson & Johnson Baby Products Company, New Brunswick, N.J.

[21] Appl. No.: 837,639

[22] Filed: Mar. 10, 1986

[51] Int. Cl.$^4$ .......................... C11D 1/18; C11D 1/12
[52] U.S. Cl. .................................... 252/542; 252/545;
 252/546; 252/551; 252/DIG. 5; 252/DIG. 15;
 252/142; 424/70
[58] Field of Search ............... 252/545, 551, 542, 546,
 252/DIG. 15, DIG. 5, 142; 568/625; 424/70

[56] References Cited

U.S. PATENT DOCUMENTS

| Re. 30,641 | 6/1981 | Verdicchio | 252/545 |
|---|---|---|---|
| 3,055,836 | 9/1962 | Masci et al. | 252/545 |
| 3,928,251 | 12/1975 | Bolich et al. | 252/545 |
| 4,299,994 | 11/1981 | Stahel | 252/DIG. 1 |
| 4,395,364 | 7/1983 | Murata et al. | 252/551 |

Primary Examiner—Josephine L. Barr
Attorney, Agent, or Firm—Steven P. Berman

[57] ABSTRACT

Detergent and cleansing compositions comprising at least one sulfated polyoxyalkylene condensation product and at least one amphoteric surfactant are provided.

10 Claims, No Drawings

DETERGENT COMPOSITIONS

BACKGROUND OF THE INVENTION

Detergent and cleansing compositions intended for use as personal cleansing products not only must exhibit good cleansing and foam characteristics but they must also be non-irritating or have low irritation potential to the skin and the eyes.

Synthetic detergents which are useful in such detergent and cleansing compositions are well known in the art and include anionic, cationic, amphoteric and nonionic detergents or surfactants, as they are usually referred to. It is desirable that detergent and cleansing compositions have good foam volume and good foam stability, particularly if they are to be used as shampoos. The amount of foam generated by a shampoo composition has a direct bearing on the perceived efficiency with which it cleans the hair. The stability of the foam generated provides an indication to the user as to how long it will keep the hair lathered. Generally speaking, the greater the volume of foam produced and the more stable the foam, the more efficient the perceived cleansing action of the shampoo. In addition, other detergent and cleansing compositions, such as liquid skin cleansers and baby bath compositions, are enhanced by high foam volume and good foam stability.

The surfactants generally exhibiting the more superior properties in terms of foaming, cleaning and end result attributes are the anionic detergents. Thus, most detergent and cleansing formulations intended for personal use contain anionic surfactants as one of the active ingredients. These surfactants, however, have a tendency to be very irritating to the skin and the eyes in the levels normally utilized, i.e., above 10% by weight of the total composition. For this reason, detergent compositions intended for personal use containing anionic surfactants are modified by substituting a significant amount of nonionic surfactants which are generally mild although of less effective foaming and cleansing ability. Certain amphoteric surfactants have also been reported to have a low eye irritation potential. Although numerous detergent and cleansing compositions are available commercially, there is still a need for compositions in which irritancy can be substantially eliminated without sacrificing other desired properties such as cleansing and foaming attributes.

In the prior art, attempts to achieve such low ocular irritating compositions have been described, such as by Masci et al. in U.S. Pat. No. 3,055,836, Bolich et al. in U.S. Pat. No. 3,928,521 and Verdicchio et al. in U.S. Pat. No. Re. 30,641. Such compositions have contained either an amphoteric/anionic reaction product or a betaine/sultaine-anionic blend in combination with an ethoxylated nonionic, but such formulations have generally exhibited inferior foam volume and stability when compared to traditional shampoo formulations.

It is, therefore, an object of this invention to provide improved detergent and cleansing compositions.

It is a further object of this invention to provide improved detergent and cleansing compositions which exhibit low irritation potential to the eyes and skin.

It is a still further object of this invention to provide improved detergent and cleansing compositions which exhibit good foaming properties including excellent foam stability.

These and other objects of the present invention will become apparent to one skilled in the art from the detailed description given hereinafter.

SUMMARY OF THE INVENTION

This invention encompasses detergent and cleansing compositions comprising as the active ingredients at least one anionic surfactant and at least one amphoteric surfactant. The balance of the compositions can comprise various detergent and cleansing adjuncts, fillers, carriers and the like which are well-known in the art.

DETAILED DESCRIPTION OF THE INVENTION

The detergent and cleansing compositions of the present invention comprise as the active ingredients at least one specific anionic surfactant and at least one amphoteric surfactant.

The anionic surfactants which are useful in the compositions of the present invention are sulfated polyoxyalkylene condensation products of the formula

wherein R is straight or branched chain alkyl of from about 6 to 10 carbon atoms; M is selected from Na, K, Mg, Ca, Al or alkanolamine; m is an integer of from about 1 to 4 and n is an integer of from about 1 to 10.

These anionic surfactants can be prepared by sulfating the polyoxyalkylene condensation products disclosed in U.S. Pat. No. 4,299,994. This patent discloses compounds of the formula

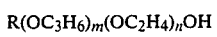

wherein R is the residue of a mixture of primary aliphatic alcohols, at least 70 mol% of which is branched 1-decanols; m is 1-4 and n is 3-20. These polyoxyalkylene condensation products can be prepared by reacting a suitable alcohol with propylene oxide to form a propoxylated alcohol which is then reacted with ethylene oxide. In order to form the anionic surfactants of the present invention, these alkylene condensation products are sulfated using conventional sulfation techniques involving $SO_3$, chlorosulfonic acid or oleum sulfation. This results in the formation of the alkylalkoxylated sulfuric acid ester which can be neutralized with the appropriate base, e.g., NaOH, amine and the like.

Specific examples of these useful sulfated anionic compounds include isodecyl-propoxy(1)-ethoxy(4) sodium sulfate, isodecyl-propoxy(2)-ethoxy(4) sodium sulfate, isoctyl-propoxy(1)-ethoxy(2) sodium sulfate and isohexylpropoxy(10)ethoxy(1)sodium sulfate. These compounds should be utilized in detergent compositions in from about 1.0 to 20.0%, preferably from about 2.0 to 6.0%.

If desired, other anionic surfactants may be utilized in combination with the above-identified anionic surfactants. Suitable anionic surfactants include salts of alkylether sulfates, alkyl sulfates, sulfosuccinates, acyl sarcosinates, olefin sulfonates and alkane sulfonates. The total anionic surfactant concentration in the compositions should be from about 1.0 to 20.0%.

The amphoteric surfactants which are useful in the compositions of the present invention may be ampholytic or zwitterionic and include betaines, sultaines, imidazolines, phosphobetaines, phosphitaines and pyrophosphobetaines.

The betaine and sultaine surfactants useful in this invention are described in U.S. Pat. No. 3,950,417 issued Apr. 13, 1976, which is incorporated herein by reference. The phosphobetaines and phosphitaines useful in this invention are described in U.S. Pat. Nos. 4,215,064 and 4,261,911 issued July 29, 1980 and Apr. 14, 1981, respectively which are incorporated herein by reference. The imidazolines which are useful in the compositions of this invention are described in U.S. Pat. No. 2,970,160, which is incorporated herein by reference and the pyrophosphobetaines useful in this invention are described in U.S. Pat. No. 4,382,036 issued May 3, 1983 which is incorporated herein by reference.

The preferred betaine amphoteric surfactants include the alkylbetaines such as cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl) carboxymethylbetaine, oleyldimethyl-gamma-carboxypropylbetaine, lauryl-bis-(2-hydroxypropyl)-carboxyethylbetaine, and the like; the sultaines such as cocodimethylpropylsultaine, stearyldimethylpropylsultaine, lauryl-bis-(2-hydroxyethyl) propylsultaine and the like; and the amidosultaines such as cocoamidodimethylpropylsultaine, stearylamidodimethylpropylsultaine, laurylamido-bis-(2-hydroxyethyl) propylsultaine, and the like.

The preferred phosphobetaines include lauric myristic amido 3-hydroxypropyl phosphobetaine, cocoamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, and the like. The preferred phosphitaines include cocoamido propyl monosodium phosphitaine, lauric myristic amido propyl monosodium phosphitaine and the like.

The preferred imidazolines include 2-cocoyl-1-(sodium carboxymethyl)-1-(2-hydroxyethyl)-2-imidazolinium chloride, 2-lauroyl-1-(sodium carboxymethyl)-1-(2-hydroxyethyl)-2-imidazolinium chloride, 2-lauroyl myristyl-1-(sodium carboxymethyl)-1-(2-hydroxyethyl)-2-imidazolinium chloride, and the like.

The preferred pyrophosphobetaines include cocoamido-3-hydroxypropyl-pyrophosphobetaine and lauric myristic-3-hydroxypropyl-pyrophosphobetaine, and the like.

The amphoteric surfactant or mixture of surfactants may be present in the compositions of the present invention in an amount of from about 1.0 to 10.0% preferably 3.0 to 7.0%. The total amount of surfactants in the compositions of the present invention should be from about 1.0 to 30.0%, depending on the desired composition.

The compositions herein also can contain a variety of non-essential optional components for rendering such compositions more stable and desirable as well as water. Such conventional optional ingredients are well-known to those skilled in the art, e.g., preservatives such as benzyl alcohol, methyl paraben, propyl paraben and imidazolicinyl urea; thickeners and viscosity modifiers such as a diethanolamide of a long chain fatty acid (e.g., coconut diethanolamide), sodium chloride, sodium sulfate, methylcellulose, polyvinyl alcohol, and ethyl alcohol; pH adjusting agents such as citric acid, succinic acid, phosphoric acid, sodium hydroxide, sodium carbonate, etc.; suspending agents such as hydrogenated castor oil; opacifiers such as ethylene glycol distearate; perfumes; dyes; conditioners such as fatty acids; and, sequestering agents such as disodium ethylenediamine tetraacetate. Such agents are used individually at a level of from about 0.1 to 5.0% by weight of the compositions. The pH of the compositions should be from about 4.0 to 9.0, preferably 6.0 to 8.0.

The compositions of the present invention may be prepared using conventional mixing and formulation techniques.

The detergent compositions of the present invention can be tested for ocular irritation by the following modified Draize Test (J. H. Draize et al., Toilet Goods Assn. No. 17, May 1952, No. 1, Proc. Sci. Sect.).

An 0.1 ml. sample of a neutral composition under test is dropped into one eye of an albino rabbit, the other eye serving as a control. Six rabbits are employed for each composition. Observations are made after 1, 24, 48, 72 and 96 hours and 7 days after initial instillation; second and third instillations are made after the 24 and 48 hour readings. Results may vary from substantially no change or only a slight irritation in the appearance of the rabbit's eye after 7 days to severe irritation and/or complete corneal opacity. Ocular lesions are scored for cornea, iris and conjuctiva with a higher number indicating greater ocular irritation and the scores are added to give a total numerical value for each reading for six rabbits and averaged. The averaged score is an indication of the irritation potential of the composition under test. Based on the averaged score, descriptive irritation evaluation may be given, e.g., none, slight, moderate, severe, as the case may be.

The detergent compositions of the present invention can be tested for eye sting potential by the following Mouse Writhing Test (R. W. Shanahan et al., J. Soc. Cosmet. Chem., 26, 581–592). A total of 10 male mice weighing between 15 and 25 grams each, 2 groups of 5 each, are used in this test for each dilution of the test sample, with four to six geometrically declining dilution (i.e. 4%, 2%, 1%, . . . ) required to obtain adequate dose-response effects. Dilutions of liquid samples are prepared in a v/v basis. Distilled water acts as the diluting agent and as the final control sample. The diluted samples are kept in stoppered serum bottles, and should be shaken vigorously prior to testing. Working with one dilution at a time, 5 mice are consecutively injected intraperitoneally with 0.22 cc of diluted sample using a 27 gauge needle attached to a one milliliter disposable tuberculin syringe. Immediately after injection, the animals are placed in a clear $18'' \times 8'' \times 8''$ polycarbonate box and observed for a maximum duration of six minutes. A stopwatch is used to keep correct time. During this time, one writhe, exhibited as a contraction of the abdominal musculature accompanied by torsion or flexion of the trunk and extension of the hind limb, is considered a positive response to pain, and the animal is removed from the box. At the end of the five minute period, this segment of the test should be terminated and 5 more animals tested at this dilution. The number of positive responses in 10 animals should be recorded, and the next dilution then tested using the same procedure. The number of positive responses seen in your first test dilution will determine whether to test higher or lower dilutions of that test sample.

Upon conclusion of the study, the total number of responses at each dilution are recorded and the median writhing dose ($WD_{50}$) calculated according to the method of Litchfield and Wilcoxon (Litchfield et al. J. Pharm. Exp. Therapeutics, 97, 399–408) with values of 1.0 or greater indicating little or no eye sting.

Specific embodiments of the detergent and cleansing compositions prepared in accordance with the present invention are illustrated by the following representative examples. It will be understood, however, that the invention is not confined to the specific limitations set forth in the individual examples, but rather to the scope of the appended claims.

EXAMPLE I

A shampoo composition is prepared as follows:

Two hundred grams of deionized water is charged to a one liter beaker equipped with stirrer. With agitation, 200 grams of 25% lauric myristic-3-hydroxypropyl-pyrophosphobetaine are added and mixed until in solution. This is followed by the addition of 119 grams of 42% active isodecylpropoxy(1)ethoxy(4) sodium sulfate. The batch is mixed until homogeneous followed by the addition of 26 grams of polyethylene glycol 6000 distearate. The solution is heated to 65°–70° C. and held for twenty minutes after which it is cooled to 30° C. Next 1.0 grams of Dowicil 200 (Dow Chemical Company's tradename for the cis isomer of 1-(3-chloroalkyl)-3,5,7-azoneadamantine chloride) and dye and fragrance, as desired, are added followed by sufficient deionized water to bring the batch total to 1000 grams. The pH is adjusted to 7.0–7.4 with 10% HCl.

This composition has the following formulation:

|  | % wt/wt |
| --- | --- |
| lauric myristic-3-hydroxypropyl-pyrophosphobetaine | 5.00 |
| isodecyl-propoxy(1)-ethoxy(4) sodium sulfate | 5.00 |
| polyethylene glycol (6000) distearate | 2.60 |
| Dowicil 200 | 0.10 |
| dyes & fragrance | 0.25 |
| deionized water | q.s. to 100 |

The pH is adjusted to 7.08 with hydrochloric acid and the viscosity at 25° C. is 1000 cps.

EXAMPLE II

A shampoo composition is prepared in accordance with Example I and has the following formulation:

|  | % wt/wt |
| --- | --- |
| cocoamido-3-hydroxypropyl-pyrophosphobetaine | 2.50 |
| laurylamidopropylbetaine | 2.50 |
| isodecyl propoxy(1)-ethoxy(4) sodium sulfate | 5.00 |
| polyethylene glycol (6000) distearate | 2.60 |
| Dowicil 200 | 0.10 |
| dye, fragrance | 0.25 |
| deionized water | q.s. to 100 |

The pH is adjusted to 7.04 with citric acid and the viscosity at 25° C. is 1400 cps.

EXAMPLE III

A shampoo composition is prepared in accordance with Example I and has the following formulation:

|  | % wt/wt |
| --- | --- |
| lauric myristic imidazoline | 5.00 |
| isodecyl-propoxy(2)-ethoxy(4) sodium sulfate | 5.00 |
| polyethylene glycol (6000) distearate | 2.60 |
| Dowicil 200 | 0.10 |
| dyes, fragrance | 0.25 |
| deionized water | q.s. to 100 |

The pH is adjusted to 7.12 with hydrochloric acid and the viscosity is 1375 cps.

EXAMPLE IV

The compositions of Examples I–III are tested for eye irritancy in accordance with the procedure of the modified Draize test described above and the following results are obtained.

| Example | 1 Hr. | Average Daily Scores | | | | | Rating |
| --- | --- | --- | --- | --- | --- | --- | --- |
|  |  | 1 Day | 2 Days | 3 Days | 4 Days | 7 Days |  |
| I | 9.8 | 2.7 | 6.7 | 9.6 | 2.8 | 0.0 | Slight/Moderate |
| II | 14.5 | 3.0 | 5.8 | 8.2 | 7.2 | 0.3 | Moderate |
| III | 10.8 | 2.7 | 4.0 | 4.3 | 3.7 | 0.0 | Slight |

EXAMPLE V

The composition of Example I is tested for human eye sting potential in accordance with the mouse writhing test procedure described above and achieved a $WD_{50}$ score of 1.74 indicating little or no potential for eye sting.

EXAMPLES VI–IX

Additional shampoo compositions are prepared in accordance with the procedure set forth in Example I and have the following formulations.

|  | % Wt/Wt | | | |
| --- | --- | --- | --- | --- |
|  | VI | VII | VIII | IX |
| isodecyl propoxy(2)-ethoxy(4) sodium sulfate | 5.00 | 5.00 | 5.00 | 5.00 |
| monolauryl sodium sulfosuccinate | 2.50 | 5.00 | — | — |
| lauric imidazoline | 2.50 | — | 5.00 | 5.00 |
| coconut fatty acid | 1.50 | 1.50 | 1.50 | — |
| lauric diethanolamide | — | — | — | 1.50 |
| polyethylene glycol 6000 distearate | 2.60 | 2.60 | 2.60 | 2.60 |
| Dowicil 200 | .10 | .10 | .10 | .10 |
| dye, fragrance | .22 | .22 | .22 | .22 |
| deionized water | qs 100% | qs 100% | qs 100% | qs 100% |
|  | pH = 7.0 | pH = 7.1 | pH = 7.5 | pH = 6.5 |

What is claimed is:

1. A detergent and cleansing composition wherein the active ingredients comprise from about 1 to 20% by weight of at least one anionic surfactant of the formula

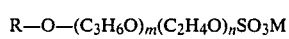

R—O—$(C_3H_6O)_m(C_2H_4O)_n$SO$_3$M wherein R is straight or branched chain alkyl of from about 6 to 10 carbon atoms; M is selected from Na, K, Mg, Ca, Al or alkanolamine; m is an integer of from about 1 to 4 and n is an integer of from about 1 to 10 and from about 1 to 10% by weight of at least one amphoteric surfactant wherein the composition has a pH of from about 4.0 to 9.0.

2. The composition of claim 1 wherein the amphoteric surfactant is selected from the group consisting of betaines, sultaines, imidazolines, phosphobetaines, phosphitaines and pyrophosphobetaines.

3. The composition of claim 2 wherein the amphoteric surfactant is a betaine.

4. The composition of claim 2 wherein the amphoteric surfactant is a sultaine.

5. The composition of claim 2 wherein the amphoteric surfactant is an imidazoline.

6. The composition of claim 2 wherein the amphoteric surfactant is a phosphobetaine.

7. The composition of claim 2 wherein the amphoteric surfactant is a phosphitaine.

8. The composition of claim 2 wherein the amphoteric surfactant is a pyrophosphobetaine.

9. The composition of claim 1 wherein the anionic surfactant is selected from the group consisting of isodecyl-propoxy(1)-ethoxy(4) sodium sulfate and isoctyl-propoxy(1)-ethoxy(2) sodium sulfate.

10. The composition of claim 1 containing from about 0 to 20.0% by weight of an anionic surfactant selected from the group consisting of alkylether sulfates, alkyl sulfates, sulfosuccinates, acyl sarcosinates, olefin sulfonates and alkane sulfonates.

* * * * *